US010981139B2

(12) United States Patent
Huang et al.

(10) Patent No.: US 10,981,139 B2
(45) Date of Patent: Apr. 20, 2021

(54) SEMICONDUCTOR QUANTUM DOT AND METHOD OF CARRYING OUT CHEMICAL REACTION OR PHOTOLUMINESCENCE REACTION BY USING THE SAME

(71) Applicants: NATIONAL CHENG KUNG UNIVERSITY, Tainan (TW); National Cheng Kung University Hospital, Tainan (TW)

(72) Inventors: Wei-lun Huang, Tainan (TW); Wu-chou Su, Tainan (TW); Hai-wen Chen, Tainan (TW); Te-fu Yeh, Tainan (TW); Hsisheng Teng, Tainan (TW); Chung-jen Chung, Tainan (TW)

(73) Assignees: NATIONAL CHENG KUNG UNIVERSITY, Tainan (TW); NATIONAL CHENG KUNG UNIVERSITY HOSPITAL, Tainan (TW)

(*) Notice: Subject to any disclaimer, the term of this patent is extended or adjusted under 35 U.S.C. 154(b) by 43 days.

(21) Appl. No.: 16/572,785

(22) Filed: Sep. 17, 2019

(65) Prior Publication Data
US 2020/0009526 A1 Jan. 9, 2020

Related U.S. Application Data

(63) Continuation of application No. 14/856,081, filed on Sep. 16, 2015, now abandoned.
(Continued)

(51) Int. Cl.
B01J 19/08 (2006.01)
H01L 31/12 (2006.01)
(Continued)

(52) U.S. Cl.
CPC ............. *B01J 19/087* (2013.01); *B01J 19/10* (2013.01); *B01J 19/123* (2013.01); *B01J 19/127* (2013.01);
(Continued)

(58) Field of Classification Search
CPC ........ B01J 19/087; B01J 19/10; B01J 19/123; B01J 2219/085; C09K 11/00; H01L 31/125; H01L 33/06
(Continued)

(56) References Cited

U.S. PATENT DOCUMENTS 6,869,864 B2  3/2005 Yim et al.
9,237,658 B2  1/2016 Dai et al.
(Continued)

FOREIGN PATENT DOCUMENTS

CN     103359727 A    10/2013

OTHER PUBLICATIONS

David Schrama et al., Antibody targeted drugs as cancer therapeutics, article, Feb. 2006, pp. 147-159, vol. 5, Nature Reviews, Drug Discovery.
(Continued)

Primary Examiner — Thinh T Nguyen
(74) Attorney, Agent, or Firm — Hauptman Ham, LLP

(57) ABSTRACT

A semiconductor quantum dot is provided with a non-metallic substrate, and has a particle size ranged from 0.3 to 100 nm. A method of carrying out a chemical reaction or a photoluminescence reaction by using the semiconductor quantum dot is also provided. A redox reaction of a target sample is carried out, an active substance is generated, or an electron-hole pair is produced from the semiconductor quantum dot by providing the semiconductor quantum dot with
(Continued)

a predetermined energy. Photons are released by the combination of the electron-hole pair so as to perform the photoluminescence reaction.

18 Claims, 16 Drawing Sheets

Related U.S. Application Data

(60) Provisional application No. 62/052,884, filed on Sep. 19, 2014.

(51) Int. Cl.
| | |
|---|---|
| C09K 11/00 | (2006.01) |
| B01J 19/10 | (2006.01) |
| B01J 19/12 | (2006.01) |
| G01N 33/58 | (2006.01) |
| B01J 35/00 | (2006.01) |
| B01J 27/24 | (2006.01) |
| B01J 23/745 | (2006.01) |
| B01J 21/18 | (2006.01) |
| B01J 21/06 | (2006.01) |

(52) U.S. Cl.
CPC ........... *B01J 19/128* (2013.01); *B01J 35/004* (2013.01); *C09K 11/00* (2013.01); *G01N 33/588* (2013.01); *H01L 31/125* (2013.01); *B01J 21/06* (2013.01); *B01J 21/18* (2013.01); *B01J 23/745* (2013.01); *B01J 27/24* (2013.01); *B01J 2219/085* (2013.01); *B01J 2219/0892* (2013.01)

(58) Field of Classification Search
USPC .............................................. 438/22; 257/13
See application file for complete search history.

(56) References Cited

U.S. PATENT DOCUMENTS

| | | |
|---|---|---|
| 9,527,741 B2 | 12/2016 | Kumar et al. |
| 9,528,192 B1 | 12/2016 | Chen |
| 2007/0292896 A1* | 12/2007 | Strano et al. ................ 435/7.9 |
| 2009/0087493 A1 | 4/2009 | Dai et al. |
| 2011/0045523 A1 | 2/2011 | Strano et al. |
| 2012/0153772 A1 | 6/2012 | Landa et al. |
| 2013/0149211 A1 | 6/2013 | Bielawski et al. |
| 2013/0184144 A1 | 7/2013 | Liang et al. |
| 2014/0081067 A1 | 3/2014 | Tour et al. |
| 2014/0145145 A1 | 5/2014 | Lee et al. |
| 2014/0225039 A1 | 8/2014 | Chiang et al. |
| 2014/0234856 A1 | 8/2014 | Reuel et al. |
| 2014/0255822 A1 | 9/2014 | Asefa et al. |
| 2014/0329002 A1 | 11/2014 | Kumar et al. |
| 2015/0080251 A1 | 3/2015 | Min et al. |
| 2015/0298977 A1 | 10/2015 | Yoon |
| 2016/0033839 A1 | 2/2016 | Lee et al. |
| 2016/0240861 A1 | 8/2016 | Kurungot et al. |
| 2016/0293347 A1 | 10/2016 | Guo et al. |
| 2016/0351738 A1 | 12/2016 | Choi et al. |
| 2017/0056859 A1 | 3/2017 | Kim et al. |
| 2017/0314141 A1 | 11/2017 | Xu |

OTHER PUBLICATIONS

Hongguang Sun et al., Oligonucleotide Aptamers: New Tools for Targeted Cancer Therapy, article, 2014, pp. 1-14, The American Society of Gene & Cell Therapy.

Carl Nathan et al., Beyond oxidative stress: an immunologist's guide to reactive oxygen species, article, May 2013, pp. 349-361, vol. 13, Nature Reviews, Immunology.

Carl Nathan, Neutrophils and immunity: challenges and opportunities, article, Mar. 2006, pp. 173-182, vol. 6, Nature Publishing Group.

Dunyaporn Trachootham et al., Targeting cancer cells by ROS-mediated mechanisms: a radical therapeutic approach?, article, Jul. 2009, pp. 579-591, vol. 8, Nature Reviews, Drug Discovery, Macmillan Publishers Limited.

Te-Fu Yeh et al., Nitrogen-Doped Graphene Oxide Quantum Dots as Photocatalysts for Overall Water-Splitting under Visible Light Illumination, article, 2014, pp. 3297-3303, Wiley-VCH Verlag GmbH & Co. KGaA, Weinheim.

Preparation and Application of Carbon Nanoparticle Diode, 69 pages.

Ryosuke Kawakami et al., Visualizing hippocampal neurons with in vivo two-photon microscopy using a 1030 nm picosecond pulse laser, report, published Jan. 24, 2013, pp. 1-7, Scientific Reports.

Hiroyuki Tetsuka et al, Advanced Materials, "Optically Tunable Amino-Functionalized Graphene Quantum Dots," Jul. 25, 2012, p. 5333-5338, vol. 24.

Chaofan Hu et al., Journal of Materials Chemistry B, "One-step preparation of nitrogen-doped graphene quantum dots from oxidized debris of graphene oxide," Oct. 30, 2012, p. 39-42, vol. 1.

Fei Liu et al., Facile Synthetic Method for Pristine Graphene Quantum Dots and Graphene Oxide Quantum Dots: Origin of Blue and Green Luminescence, Adv. Mater. 2013, p. 3657-3662, vol. 25, Wiley-VCH Verlag GmbH & Co. KGaA, Weinheim, Germany.

Y. Wang et al., "Nanometer-Sized Semiconductor Clusters: Materials Synthesis, Quantum Size Effects, and Photophysical Properties", The Journal of Physical Chemistry, vol. 95, No. 2, 1991, pp. 525-532.

\* cited by examiner

US 10,981,139 B2

SEMICONDUCTOR QUANTUM DOT AND METHOD OF CARRYING OUT CHEMICAL REACTION OR PHOTOLUMINESCENCE REACTION BY USING THE SAME

CROSS REFERENCE TO RELATED APPLICATIONS

This application is a continuation application of U.S. patent application Ser. No. 14/856,081, filed on Sep. 16, 2015, and claims the benefit of the filing date of U.S. provisional patent application Ser. No. 62/052,884, filed on Sep. 19, 2014, the disclosures of which are incorporated herein by reference.

FIELD OF THE INVENTION

The present invention relates to a semiconductor quantum dot and a method of carrying out a chemical reaction or a photoluminescence reaction by using the semiconductor quantum dot, and in particular relates to a semiconductor quantum dot doped with group III~VIA elements or transition elements having empty d orbitals and a method of carrying out a chemical reaction or a photoluminescence reaction by using the semiconductor quantum dot.

BACKGROUND OF THE INVENTION

The conventional metallic semiconductor quantum dots, such as titanium dioxide ($TiO_2$), or cadmium sulfide (CdS), can be used for converting light energy to generate electron-hole pairs (or redox pairs) in the light, and catalyze the reactant, such as water, organic pollution, ammonia, etc., to perform the oxidation-reduction reaction, and further produce hydrogen or achieve decontamination to solve energy or environmental problems by the different reactants. Furthermore, in the above photochemical reaction process, the radicals or peroxides such as $O_2\cdot$, $OH\cdot$, $H_2O_2$ are often produced, which can inhibit tumor growth or reproduction of bacteria, and therefore can be applied to the treatment. The electron-hole pairs generated by light can be recombined to release photons, and carry out a photoluminescence reaction used in detection of the target (such as a specific cell, tissue, or microorganism) for assisting diagnosis.

The current metallic semiconductor quantum dots, such as titanium dioxide, have disadvantages as following: (1) In the application of photochemical reactions of solar energy, the absorption range is ultraviolet light (wavelength less than 380 nm) of sunlight. The absorbed energy is only 4 percent of sunlight, and unable to effectively improve the efficiency. (2) Since the titanium dioxide quantum dots are very stable, and not easy to change the electronic properties by surface modification, it is not conducive to biomedical diagnosis and treatment of specific target design, and other applications in development related components. (3) In the treatment, since the penetration of ultraviolet light is very poor for skin, the UV excitation produces a low concentration of free radicals in the human body for carrying out the photochemical reactions. Therefore, the inhibition effect of tumor growth or bacterial growth is very limited. (4) In the diagnosis, titanium dioxide is a very stable quantum dot, the redox pairs generated under the light irradiation can be stably stored in the titanium dioxide, it is difficult to re-combine to release photons, and therefore the target position (such as a specific cell, tissue and microbial) cannot be effectively detected for assisting the diagnosis.

Moreover, another general metallic semiconductor quantum dots, such as cadmium sulfide, have disadvantages as following: (1) In photo catalysis, although the absorption range can be extended to infrared light (wavelength less than 700 nm), the cadmium sulfide quantum dots are easy to be oxidized by the generated redox pairs under light irradiation and cause photo corrosion. The catalysis reaction cannot be performed stably. (2) In the treatment, although the red to near-infrared light having strong penetration can be used as a light source, however, the generation efficiency of the free radicals or peroxides, such as $O_2\cdot$, $OH\cdot$, $H_2O_2$, is very low, so that the treatment effect is poor. (3) Metal cadmium has high bio-toxicity, and is not suitable for diagnosis and treatment in vivo. (4) When applying to the diagnosis, since the CdS quantum dots have poor hydrophilicity, they need to perform a tedious surface modification before they can be uniformly dispersed in water. The process complexity is increased, the yield is declined, costs are increased, and the stability in water phase is affected, which are against their biomedical applications. (5) The CdS is difficult to be connected with biological molecules (such as antibodies, proteins, nucleic acids and lipids, etc.), resulting in a hard modification of specificity. (6) The surface of the CdS quantum dots contains many defects, and it is hard to carry out a photoluminescence reaction under a light irradiation. It is necessary to design a core-shell type composite or perform a complex surface modification to remove the defect so as to enhance the irradiation efficiency, but the complexity and the cost of the process are also increased.

As described above, although the conventional metallic semiconductor quantum dots also have the ability to provide the electron-hole pairs in the conversion of light energy to carry out a chemical reaction or photoluminescence reaction, however, the material properties, absorbance capacity, energy conversion efficiency, toxicity, chemical modification of the conventional metallic semiconductor quantum have the congenital obstacles which are insurmountable, therefore its scope of application is limited.

It is therefore necessary to provide a semiconductor quantum dot and a method of carrying out a chemical reaction or a photoluminescence reaction by using the semiconductor quantum dot, in order to solve the problems existing in the conventional technology as described above.

SUMMARY OF THE INVENTION

A primary object of the present invention is to provide a semiconductor quantum dot and a method of carrying out a chemical reaction or a photoluminescence reaction by using the semiconductor quantum dot. The semiconductor quantum dot has a substrate without any metal element itself, and has the electronic structure capable of being modified by adjusting the size to have light absorption from ultraviolet to infrared (wavelength greater than 200 nm and less than 1400 nm) and generate a large number of electron-hole pairs, so as to provide more driving force for performing a redox reaction. Moreover, when providing energy for a long time, the corrosion is not easy to occur, and thus the electron-hole pairs can be provided stably for the redox reaction or the photoluminescence reaction. In addition, compared with the traditional metallic semiconductor quantum dot, the semiconductor quantum dot has better bio-compatibility due to the included elements, and has lower bio-toxicity after surface modification or doping with non-metallic elements. Therefore, the semiconductor quantum dot is more secure for organisms (especially human). On the other hand, when the semiconductor quantum dot is not used in vivo, or used in some special applications in vivo, the doped transition elements having empty d orbitals can provide a stronger chemical reaction or photoluminescence reaction, or have additional functions. This semiconductor quantum dot is a multi-functional platform having extremely high flexibility to be suitable for use in biomedical or non-biomedical applications.

To achieve the above object, the present invention provides a semiconductor quantum dot, comprising a non-metallic substrate, and having a particle size ranged from 0.3 nm to 100 nm.

In one embodiment of the present invention, the non-metallic substrate is made of a group IVA element.

In one embodiment of the present invention, the non-metallic substrate is a carbon-based material or a silicon-based material.

In one embodiment of the present invention, the carbon-based material is graphene or graphene oxide.

In one embodiment of the present invention, the semiconductor quantum dot comprises at least one dopant.

In one embodiment of the present invention, the dopant is selected from at least one of group IIIA element, group IVA element, group VA element, group VIA element, and transition element having an empty d orbital.

In one embodiment of the present invention, the dopant is O, N, P, B, Fe, Co, or Ni.

In one embodiment of the present invention, the dopant has a doping ratio more than 0 mol % and less than 50 mol %.

In one embodiment of the present invention, the semiconductor quantum dot is disc-shaped, and has a thickness ranged from 0.1 nm to 10 nm.

In one embodiment of the present invention, the surface of the non-metallic substrate has at least one functional group selected from H, a group-VA-element functional group, or a group-VIA-element functional group.

In one embodiment of the present invention, the group-VA-element functional group is an amino group, P, or a phosphate group.

In one embodiment of the present invention, the group-VIA-element functional group is hydroxyl, carbonyl, carboxyl, or acyl.

In one embodiment of the present invention, the semiconductor quantum dot generates electron-hole pairs or redox pairs by receiving a predetermined energy, so as to catalyze a redox reaction, or to release photons by combining the electron-hole pairs to perform a photoluminescence reaction.

In one embodiment of the present invention, the predetermined energy is electromagnetic energy, light, electricity, heat, magnetic energy or ultrasound.

In one embodiment of the present invention, the photoluminescence reaction releases a light having a wavelength ranged from 250 nm to 1600 nm.

Furthermore, the present invention provides a method of carrying out a chemical reaction by using a semiconductor quantum dot, comprising steps of (1) mixing a target sample with the abovementioned semiconductor quantum dot, wherein the semiconductor quantum dot comprises oxidized graphene oxide and has a particle size ranging from 0.3 to 100 nm; and (2) providing the semiconductor quantum dot with a predetermined energy, so that the semiconductor quantum dot generates electron-hole pairs, and a redox reaction of the target sample is carried out by the electron-hole pairs; or the target sample or a surrounding molecule thereof generates an active substance, and a redox reaction of the target sample is carried out by the active substance.

In one embodiment of the present invention, the semiconductor quantum dot comprises at least one dopant.

In one embodiment of the present invention, the dopant is selected from at least one of group IIIA element, group IVA element, group VA element, group VIA element, and transition element having an empty d orbital.

In one embodiment of the present invention, the dopant is at least one of O, N, P, B, Fe, Co, and Ni.

In one embodiment of the present invention, the dopant has a doping ratio more than 0 mol % and less than 50 mol %.

In one embodiment of the present invention, the semiconductor quantum dot is disc-shaped, and has a thickness ranged from 0.1 nm to 10 nm.

In one embodiment of the present invention, the semiconductor quantum dot has a surface with at least one functional group selected from H, a group-VA-element functional group, or a group-VIA-element functional group.

In one embodiment of the present invention, the group-VA-element functional group is an amino group, P, or a phosphate group.

In one embodiment of the present invention, the group-VIA-element functional group is hydroxyl, carbonyl, carboxyl, or acyl.

In one embodiment of the present invention, the predetermined energy is provided by a laser, a mercury lamp, a visible light, an ultraviolet light, an infrared light, an endoscopic light, an X-ray, an ultrasound, an electric field, a magnetic field, a nuclear magnetic resonance, or a light-emitting diode in the step (2).

In one embodiment of the present invention, the redox reaction in the step (2) comprises decomposition of the target sample, polymerization of the target sample, activation of the target sample, or deactivation of the target sample.

In one embodiment of the present invention, the active substance is a free radical or a peroxide.

In one embodiment of the present invention, the free radical is $O_2\cdot$ or $OH\cdot$; and the peroxide is $H_2O_2$.

In one embodiment of the present invention, the target sample is selected from biological cells, bacteria, viruses, parasites, cell secretions, biological molecules, an organic compound, or an inorganic compound.

In one embodiment of the present invention, the organic compound is an aromatic compound, alcohol, aldehyde, ketone, acid, amine, urea, or a polymer thereof.

In one embodiment of the present invention, the inorganic compound is water, nitrite, nitrate or ammonia.

In one embodiment of the present invention, the biological molecules are peptides, nucleic acids, lipids, carbohydrates, vitamins, hormones, or a polymer thereof.

In one embodiment of the present invention, the cell secretions are extracellular vesicles or extracellular matrix.

Furthermore, the present invention provides a method of carrying out a photoluminescence reaction by using a semiconductor quantum dot, comprising steps of (1) delivering the semiconductor quantum dot to a predetermined position, wherein the semiconductor quantum dot comprises oxidized graphene oxide and has a particle size ranging from 0.3 to 100 nm; and (2) providing the semiconductor quantum dot with a predetermined energy, so that the semiconductor quantum dot generates electron-hole pairs, and releases photons by combining the electron-hole pairs to perform the photoluminescence reaction.

In one embodiment of the present invention, the predetermined energy is provided by a laser, a mercury lamp, a visible light, an ultraviolet light, an infrared light, an endoscopic light, an X-ray, an ultrasound, an electric field, a magnetic field, a nuclear magnetic resonance, or a light-emitting diode in the step (2).

In one embodiment of the present invention, the photoluminescence reaction has a wavelength ranged from 250 nm to 1600 nm.

In one embodiment of the present invention, the method comprises a step (3) of using the photoluminescence reaction as being a signal source after the step (2).

DESCRIPTION OF THE DRAWINGS

FIGS. 7a to 7c) prepared by different process according to the Embodiment 2-4 of the present invention, and the boron-doped graphene oxide quantum dots (BGOQD: FIG. 7d) according to the Embodiment 2-2 of the present invention providing with UV energy (FIG. 7e).

DETAILED DESCRIPTION OF THE PREFERRED EMBODIMENTS

Figure 1A:
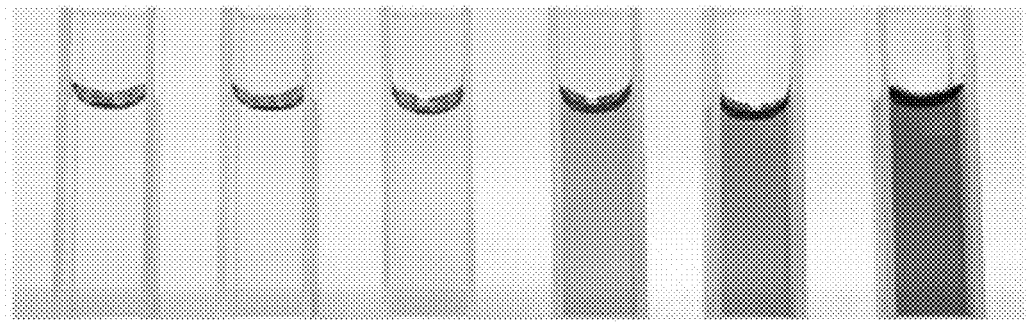
FIGS. 1a to 1b show the photoluminescence reaction having different colors generated by the amino-nitrogen-doped graphene oxide quantum dots after irradiating with UV light according to the Embodiment 3-2 of the present invention.

The structure and the technical means adopted by the present invention to achieve the above and other objects can be best understood by referring to the following detailed description of the preferred embodiments. In addition, directional terms described by the present invention, such as upper, lower, front, back, left, right, inner, outer, side, etc., are only directions by referring to the accompanying drawings, and thus the directional terms are used to describe and understand the present invention, but the present invention is not limited thereto. Furthermore, if there is no specific description in the invention, singular terms such as "a", "one", and "the" include the plural number. For example, "a compound" or "at least one compound" may include a plurality of compounds, and the mixtures thereof. If there is no specific description in the invention, the "%" means "weight percentage (wt %)", and the numerical range (e.g. 10%~11% of A) contains the upper and lower limit (i.e. 10%≤A≤11%). If the lower limit is not defined in the range (e.g. less than, or below 0.2% of B), it means that the lower limit is 0 (i.e. 0% ≤B ≤0.2%). The proportion of "weight percent" of each component can be replaced by the proportion of "weight portion" thereof. The abovementioned terms are used to describe and understand the present invention, but the present invention is not limited thereto.

The present invention provides a semiconductor quantum dot, comprising a non-metallic substrate, and having a particle size ranged from 0.3 nm to 100 nm , such as 0.5, 1, 5, 15, or 50 nm, but it is not limited thereto. The non-metallic substrate can be made of a group IVA element, such as a carbon-based material or a silicon-based material. Preferably, the carbon-based material is graphene or graphene oxide. Additionally, the shape of the semiconductor quantum dot is substantially determined by the shape of the non-metallic substrate, which generally presents a ball-shaped structure, but the other shape such as pillar-shaped or disc-shaped is possible. Preferably, when the non-metallic substrate is graphene oxide, the semiconductor quantum dot presents a disc-shaped structure having a thickness ranged from 0.1 nm to 10 nm, such as 0.5, 5, or 10 nm, but it is not limited thereto.

Furthermore, the semiconductor quantum dot can be provided with at least one dopant or doping atom at the same time, for example group IIIA, IVA, VA, VIA elements, or transition elements with empty d orbital in the periodic table. The dopant can be O, N, P, B, Fe, Co, or Ni, etc. The ratio of the dopant to the non-metallic substrate is less than 50 mol %, such as 10, 20, 30, or 40 mol %, but it is not limited thereto. In addition to the dopant, the surface of the non-metallic substrate can be modified to attach at least one functional group for various applications. The functional group can be selected from hydrogen atom, a group-VA-element functional group, or a group-VIA-element functional group, wherein the group-VA-element functional group can be an amino group (—$NH_2$), P, or a phosphate group (HOPO(OR)$_2$); the group-VIA-element functional group can be hydroxyl (—OH), carbonyl (—C═O), carboxyl (—COOH), or acyl. Through the functional group, the semiconductor quantum dot and biomolecules can be bound more easily (e.g. binding to antibodies through the amino groups) for assisting inspection, indicating positions, image diagnosis, or cancer treatment. After doping, the electronic and structural properties of the non-metallic substrate can be efficiently changed, so that the semiconductor quantum dot can absorb a light from visible light to infrared light (wavelength less than 1600 nm), and the light emission rate can also be promoted to more than 70% (by doping with N and surface modification with $NH_2$).

Another embodiment of the present invention provides a method of carrying out a chemical reaction by using a semiconductor quantum dot, mainly comprising steps of: (S1) mixing a target sample with the abovementioned semiconductor quantum dot; and (S2) providing the semiconductor quantum dot with a predetermined energy, so that the semiconductor quantum dot generates electron-hole pairs, and a redox reaction of the target sample is carried out by the electron-hole pairs; or, the target sample or a surrounding molecule thereof generates an active substance to carry out a redox reaction of the target sample by the active substance.

The principle and the implementation details of each step in this embodiment of the present invention will be described in detail hereinafter.

First, the method of carrying out a chemical reaction by using a semiconductor quantum dot according to one embodiment of the present invention is the step (S1): mixing a target sample with the abovementioned semiconductor quantum dot. In this step, the way of mixing can be determined by the type of the target sample, for example, the semiconductor quantum dot and the target sample can be uniformly dispersed in a medium (e.g. water, saline solution, ethanol, etc.), or the semiconductor quantum dot is dispersed in the medium firstly, and then the semiconductor quantum dot is introduced together with the medium to the position of the target sample.

Next, the method of carrying out a chemical reaction by using a semiconductor quantum dot according to one embodiment of the present invention is the step (S2): providing the semiconductor quantum dot with a predetermined energy, so that the semiconductor quantum dot generates electron-hole pairs, and a redox reaction of the target sample is directly carried out by the electron-hole pairs; or, the target sample or a surrounding molecule thereof generates an active substance to carry out a redox reaction of the target sample. In this step, the target sample can be selected from biological cells, bacteria, viruses, parasites, cell secretions, biological molecules, an organic compound, or an inorganic compound. Preferably, the organic compound can be an aromatic compound, alcohol, aldehyde, ketone, acid, amine, urea, or a polymer thereof; the inorganic compound can be water, nitrite, nitrate or ammonia; the biological molecules can be peptides, nucleic acids, lipids, carbohydrates, vitamins, hormones, or polymers thereof; the cell secretions can be extracellular vesicles or extracellular matrix. Additionally, the predetermined energy is provided by a light source or the other such as ultrasonic or a nuclear magnetic resonance. The light source has a wavelength ranged from 200 nm to 1400 nm, such as a laser, a mercury lamp, a visible light, an ultraviolet light, an infrared light, an endoscopic light, an X-ray, an ultrasound, an electric field, a magnetic field, a nuclear magnetic resonance, or a light-emitting diode. Preferably, the predetermined energy is provided by the visible light, the ultraviolet light, or the infrared light to directly carry out the redox reaction of the target sample, or the target sample or the surrounding molecule thereof generates the active substance to carry out a redox reaction of the target sample.

Furthermore, the redox reaction in the step (2) is mainly decomposition of the target sample, polymerization of the target sample, activation of the target sample, or deactivation of the target sample. The active substance is a free radical or a peroxide, such as $O_2 \cdot$, $OH \cdot$, $H_2O_2$, and etc.

The other embodiment of the present invention provides a method of carrying out a photoluminescence reaction by using a semiconductor quantum dot, mainly comprising steps of: (S1) delivering the abovementioned semiconductor quantum dot to a predetermined position; and (S2) providing the semiconductor quantum dot with a predetermined energy, so that the semiconductor quantum dot generates electron-hole pairs, and releases photons by combining the electron-hole pairs to perform a photoluminescence reaction. The photoluminescence reaction has a wavelength ranged from 250 nm to 1600 nm.

Furthermore, in one embodiment, a step of (S3) of using the photoluminescence reaction as being a signal source can be included after the step (S2) of the abovementioned embodiment. The signal source can be used for distinguishing a specific status, showing a specific pattern or images of the target sample by wavelengths, colors, or intensity, or providing light energy directly. For example, different biological molecules can be labeled by using different colors of fluorescent, a quantum dot display can be used for showing the patterns of the fluorescent, or applying to a LED application.

To make the semiconductor quantum dot provided by the present invention more definite, please refer to the experiment process described in the following.

Embodiment 1-1: preparation of graphene oxide quantum dot

A commercially available or self-prepared graphene oxide is oxidized in concentrated nitric acid at room temperature for 12 hours, then the mixed solution is treated with ultrasonic vibration for 10 hours, and the resulting mixture is placed in an exhaust gas recovery apparatus provided with a calcination furnace and calcined at 140° C. for 12 hours in order to exclude the concentrated nitric acid (boiling point 83° C.). The product is dispersed in 40 ml of water, and then filtered through a 0.22 μm microporous membrane and 10000 rpm of centrifugation, and the resulting black suspensions are graphene oxide quantum dots.

Embodiment 1-2: preparation of graphene oxide quantum dot 0.3 g graphene oxide and 0.25 g of sodium nitrate are weighed, and poured into 15 ml of 18M concentrated sulfuric acid solution in an ice bath. 1.5 g of potassium permanganate is added with stirring at 20° C. Then the mixture is stirred for 12 hours at 35° C. to carry out the oxidation reaction. Raising the temperature to 98° C., the mixture is stirred for 15 minutes, and 50 ml of deionized water is added. Then, at room temperature, 3 ml of 35 wt % hydrogen peroxide ($H_2O_2$) is added and continuously stirred to terminate the reaction, and then the ethanol precipitated product is repeatedly washed with ethanol, and centrifuged to obtain graphene oxide quantum dots.

Embodiment 1-3: preparation of graphene oxide quantum dot with different sizes

The graphene oxide quantum dots obtained from the Embodiment 1-1 or 1-2 are centrifugalized in a centrifuge tube having a series of different pore sizes (100 KD, 30 KD, 10 KD, 5 KD, 3 KD, 2 KD) polyethersulfone membrane. Under the centrifugal forces, the graphene oxide quantum dots with different particle sizes can be separated and obtained according to the different pore sizes.

Embodiment 1-4: preparation of graphene oxide quantum dot with different sizes

A serious concentrations of ethanol or phosphate buffered saline (PBS) is established by using the graphene oxide quantum dots obtained from the Embodiment 1-1 or 1-2. The different sized graphene oxide quantum dots are precipitated according to different concentrations of ethanol or PBS, and then the precipitated graphene oxide quantum dots are collected and obtained according to the different sizes by centrifuge.

Embodiment 2-1: preparation of nitrogen-doped graphene oxide quantum dot

The graphene oxide is placed into ammonia flow and calcined at 500° C. for 3 hours to synthesize nitrogen-doped graphene oxide. Then, the nitrogen-doped graphene oxide is oxidized in concentrated nitric acid at room temperature for 12 hours, and the mixed solution is treated with ultrasonic vibration for 10 hours, the resulting mixture is placed in an exhaust gas recovery apparatus provided with a calcination furnace and calcined at 140° C. for 12 hours in order to exclude the concentrated nitric acid (boiling point 83° C.).

The product is dispersed in 40 ml of water, and then filtered through a 0.22 μm microporous membrane and 10000 rpm of centrifugation, and the resulting brown suspensions are nitrogen-doped graphene oxide quantum dots.

Embodiment 2-2: preparation of boron-doped graphene oxide quantum dot

The boric acid is dissolved in ethanol, and then the graphene oxide is added to the mixed solution. The mixture is dried for 12 hours at 80° C., and then heated at 500° C. under argon (Ar) flow for 3 hours to synthesize boron-doped graphene oxide. Then, the boron-doped graphene oxide is oxidized in concentrated nitric acid at room temperature for 12 hours, and the mixed solution is treated with ultrasonic vibration for 10 hours, the resulting mixture is placed in an exhaust gas recovery apparatus provided with a calcination furnace and calcined at 140° C. for 12 hours in order to exclude the concentrated nitric acid. The product is dispersed in 40 ml of water, and then filtered through a 0.22 μm microporous membrane and 10000 rpm of centrifugation, and the resulting brown suspensions are boron-doped graphene oxide quantum dots.

Embodiment 2-3: preparation of iron-doped graphene oxide quantum dots

The iron oxide is dissolved in ethanol, and then the graphene oxide is added to the mixed solution. The mixture is dried for 12 hours at 80° C., and then heated at 500° C. under argon (Ar) flow for 3 hours to synthesize boron-doped graphene oxide. Then, the boron-doped graphene oxide is oxidized in concentrated nitric acid at room temperature for 12 hours, and the mixed solution is treated with ultrasonic vibration for 10 hours, the resulting mixture is placed in an exhaust gas recovery apparatus provided with a calcination furnace and calcined at 140° C. for 12 hours in order to exclude the concentrated nitric acid (boiling point 83° C.). The product is dispersed in 40 ml of water, and then filtered through a 0.22 μm microporous membrane and 10000 rpm of centrifugation, and the resulting brown suspensions are iron-doped graphene oxide quantum dots.

Embodiment 2-4: preparation of boron-and-nitrogen-doped graphene oxide quantum dot The boron-doped graphene oxide obtained from the Embodiment 2-2 is calcined at 500° C. under ammonia gas flow for 3 hours to synthesize boron-and-nitrogen-doped graphene oxide. Then, the boron-and-nitrogen-doped graphene oxide is oxidized in concentrated nitric acid at room temperature for 12 hours, and the mixed solution is treated with ultrasonic vibration for 10 hours, the resulting mixture is placed in an exhaust gas recovery apparatus provided with a calcination furnace and calcined at 140° C. for 12 hours in order to exclude the concentrated nitric acid (boiling point 83° C.). The product is dispersed in 40 ml of water, and then filtered through a 0.22 μm microporous membrane and 10000 rpm of centrifugation, and the resulting brown suspensions are boron-and-nitrogen-doped graphene oxide quantum dots.

Embodiment 2-5: preparation of nitrogen-doped graphene oxide quantum dots with different sizes The nitrogen-doped graphene oxide quantum dots obtained from the Embodiment 2-1 are centrifugalized in a centrifuge tube having a series of different pore sizes (100 KD, 30 KD, 10 KD, 5 KD, 3 KD, 2 KD) polyethersulfone membrane. Under the centrifugal forces, the nitrogen-doped graphene oxide quantum dots with different particle sizes can be separated and obtained according to the different pore sizes.

A serious concentrations of ethanol or phosphate buffered saline (PBS) is established by using the nitrogen-doped graphene oxide quantum dots obtained from the Embodiment 2-1. The different sized graphene oxide quantum dots are precipitated according to different concentrations of ethanol or PBS, and then the precipitated nitrogen-doped graphene oxide quantum dots are collected and obtained according to the different sizes by centrifuge.

Embodiment 3-1: preparation of nitrogen-doped graphene oxide quantum dot with amino groups The nitrogen-doped graphene oxide quantum dots obtained from Embodiment 2-1 are treated at 25° C. under ammonia gas flow for 12 hours, and the nitrogen-doped graphene oxide quantum dots with amino groups on the surface thereof (amino-nitrogen doped graphene oxide quantum dots) can be obtained.

Embodiment 3-2: preparation of nitrogen-doped graphene oxide quantum dot with amino groups with different sizes The amino-nitrogen-doped graphene oxide quantum dots obtained from the Embodiment 3-1 are centrifugalized in a centrifuge tube having a series of different pore sizes (100 KD, 30 KD, 10 KD, 5 KD, 3 KD, 2 KD) polyethersulfone membrane. Under the centrifugal forces, the amino-nitrogen-doped graphene oxide quantum dots with different particle sizes can be separated and obtained according to the different pore sizes.

A serious concentrations of ethanol or phosphate buffered saline (PBS) is established by using the amino-nitrogen-doped graphene oxide quantum dots obtained from the Embodiment 3-1. The different sized amino-nitrogen-doped graphene oxide quantum dots are precipitated according to different concentrations of ethanol or PBS, and then the precipitated amino-nitrogen-doped graphene oxide quantum dots are collected and obtained according to the different sizes by centrifuge.

Figure 1B:
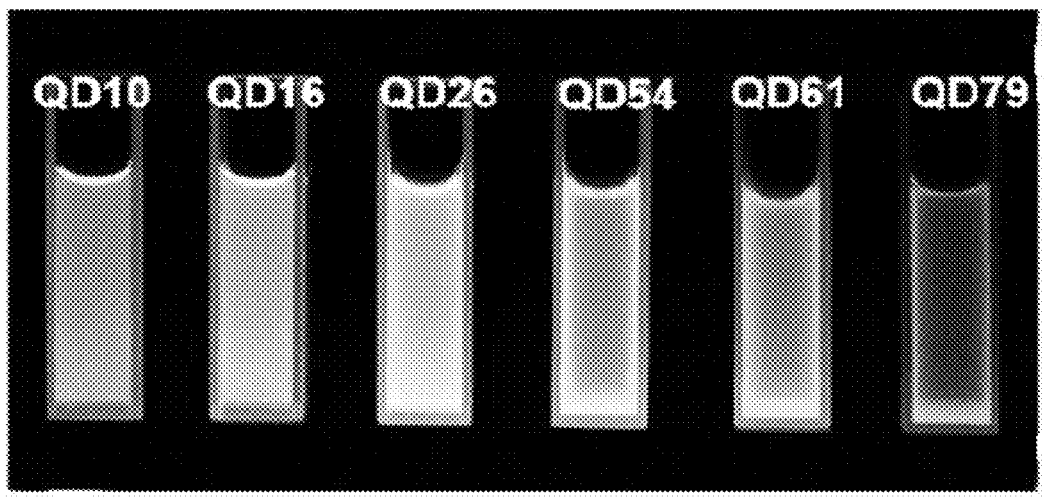

As shown in FIGS. 1a to 1b, the amino-nitrogen-doped graphene oxide quantum dots with different particle sizes according to the Embodiment 3-2 perform different colors by the photoluminescence reaction after irradiating with ultraviolet light. Please refer to FIG. 1a, different sizes amino-nitrogen-doped graphene oxide quantum dots (from left to right, from small to large diameter of 10, 16, 26, 54, 61, 79 Å) present the colors from light yellow to reddish-brown color under a visible light irradiation. Refer to FIG. 1b, after irradiating with UV irradiation with 365 nm of wavelength, different colors from blue to red fluorescence are generated.

Embodiment 4-1: preparation of silicon-based quantum dot 1.14 g of silicon tetrachloride is dissolved in 300 ml of 1,2-dimethoxyethane, and the solution containing 1.95 g of sodium sulfide in 30 ml of THF (tetrahydrofuran) is added thereto, the mixture is stirred at 35° C. for 4 hours to perform reduction and polymerization. Then 10 ml of a hexane solution containing 1.6M n-butyllithium is added to terminate the polymerization reaction. The produced mixture is washed with 500 ml of deionized water for 3 times to remove the excess salts, and the product is in an exhaust gas recovery apparatus provided with a calcination furnace and calcined at 140° C. for 12 hours in order to exclude the hexane (boiling point 68° C.). The product is dispersed in 40 ml of water, filtered through a 0.22 μm microporous membrane and 10000 rpm of centrifugation, and the silicon-based quantum dots can be obtained.

Embodiment 4-2: preparation of silicon-based quantum dots with different sizes

The silicon-based quantum dots obtained from the Embodiment 4-1 are centrifugalized in a centrifuge tube having a series of different pore sizes (100 KD, 30 KD, 10

KD, 5 KD, 3 KD, 2 KD) polyethersulfone membrane. Under the centrifugal forces, the silicon-based quantum dots with different particle sizes can be separated and obtained according to the different pore sizes.

Embodiment 5-1: preparation of nitrogen-doped silicon-based quantum dots

The silicon-based quantum dots obtained from the Embodiment 4-1 are placed into ammonia flow and calcined at 500° C. for 3 hours. Then, the mixture is oxidized in concentrated nitric acid at room temperature for 12 hours, and the mixed solution is treated with ultrasonic vibration for 10 hours, the resulting mixture is placed in an exhaust gas recovery apparatus provided with a calcination furnace and calcined at 140° C. for 12 hours in order to exclude the concentrated nitric acid (boiling point 83° C.). The product is dispersed in 40 ml of water, and then filtered through a 0.22 μm microporous membrane and 10000 rpm of centrifugation to obtain the nitrogen-doped silicon-based quantum dots.

Embodiment 5-2: preparation of iron-doped silicon-based quantum dots

The iron oxide is dissolved in ethanol, and then the silicon-based quantum dots from the Embodiment 4-1 are added to the mixed solution. The mixture is dried for 12 hours at 80° C., and then heated at 500° C. under argon (Ar) flow for 3 hours to synthesize boron-doped graphene oxide. Then, the boron-doped graphene oxide is oxidized in concentrated nitric acid at room temperature for 12 hours, and the mixed solution is treated with ultrasonic vibration for 10 hours, the resulting mixture is placed in an exhaust gas recovery apparatus provided with a calcination furnace and calcined at 140° C. for 12 hours in order to exclude the concentrated nitric acid (boiling point 83° C.). The product is dispersed in 40 ml of water, and then filtered through a 0.22 μm microporous membrane and 10000 rpm of centrifugation to obtain iron-doped silicon-based quantum dots.

Embodiment 6: preparation of nitrogen-doped silicon-based quantum dots with amino groups The nitrogen-doped silicon-based quantum dots obtained from Embodiment 5-1 are treated at 25° C. under ammonia gas flow for 12 hours, and the nitrogen-doped silicon-based quantum dots with amino groups on the surface thereof can be obtained.

Figure 2:
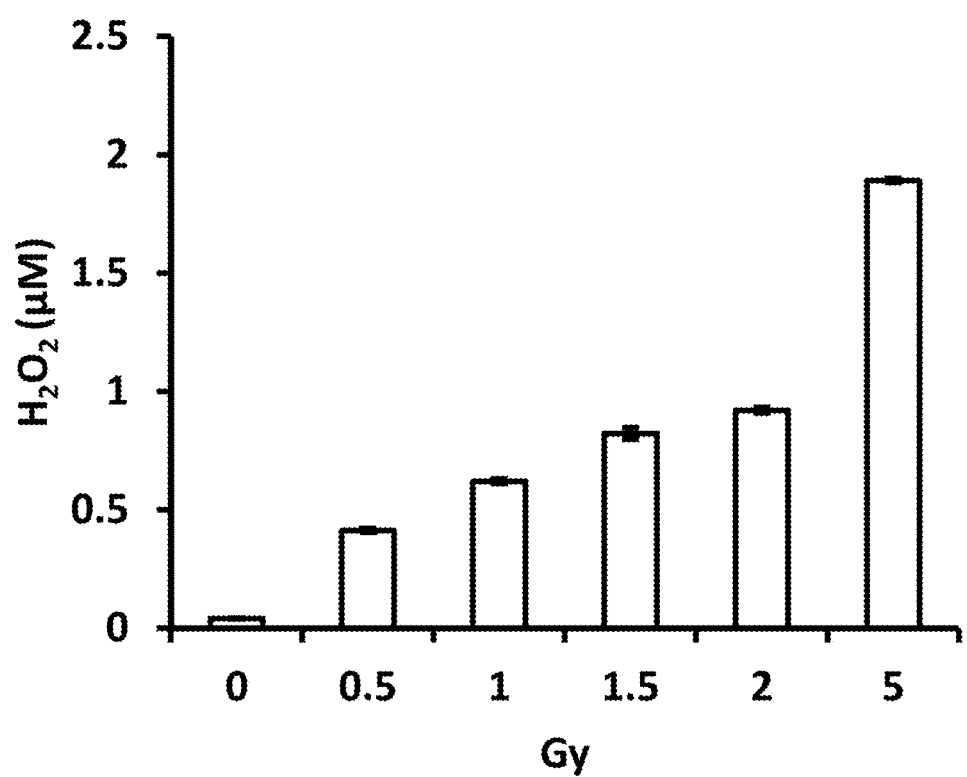
FIG. 2 is a diagram showing the concentration of the free radical of $H_2O_2$ generated from water under different doses in clinical cancer treatment, which is used for comparing with the free radical of $H_2O_2$ generated by using the semiconductor quantum dot.
Figure 3:
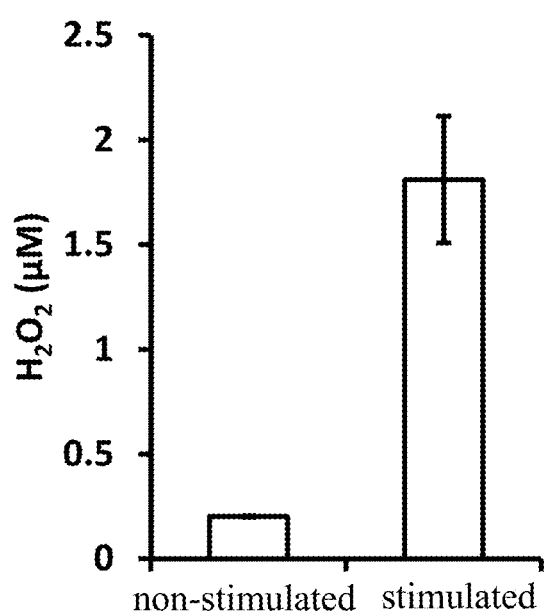
FIG. 3 shows the concentration of the free radical generated by irradiating the nitrogen-doped graphene oxide quantum dot according to the Embodiment 2-1 of the present invention under a visible light.
Figure 4A:
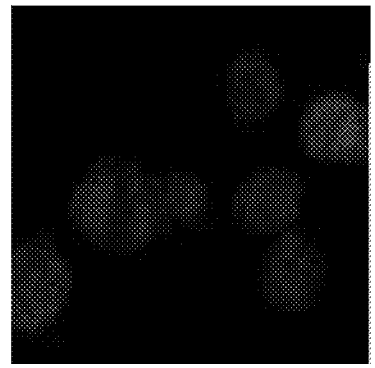
FIGS. 4a to 4f are images of the photoluminescence reaction of the amino-nitrogen-doped graphene oxide quantum dot of the Embodiment 3-2 in lung cancer cells observed with multiphoton fluorescence microscope.
Figure 4B:
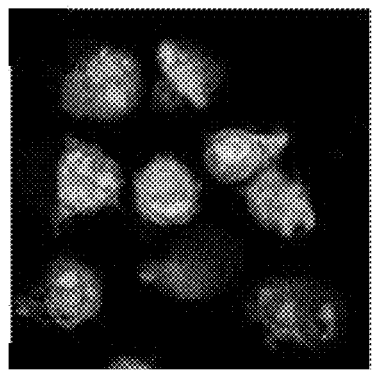
Figure 4C:
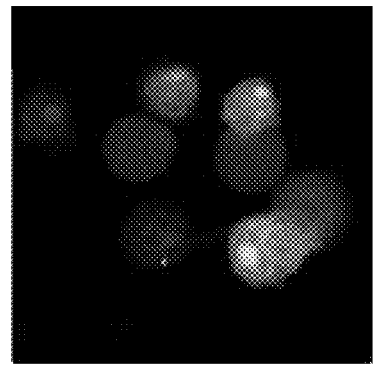
Figure 4D:
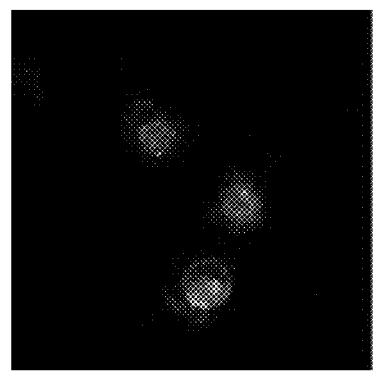
Figure 4E:
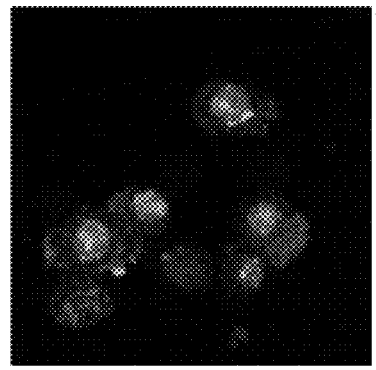
Figure 4F:

The various semiconductor quantum dot obtained from the abovementioned embodiments can be applied to generate free radicals to inhibit cancers. As shown in FIG. 2, showing the concentration of free radicals generated from water by radiation at clinically used does. It can be understood from FIG. 2 that the higher doses is necessary for generating higher concentration of the free radicals of $H_2O_2$ to achieve a better treatment effect of cancers. In addition, when the used doses reach 5 Gy, the concentration of the free radical is about 2 μM. Please refer to FIG. 3, which shows the concentration of the free radicals generated through the nitrogen-doped graphene oxide quantum dots of the Embodiment 2-1 under a visible light. In FIG. 3, the nitrogen-doped graphene oxide quantum dots are irradiated under the visible light provided by 100 W of halogen lamp for 10 mins, and the concentration of free radicals $H_2O_2$ can be generated to about 2 μM, while the free radicals $H_2O_2$ are generated slightly higher than the background value without using the nitrogen-doped graphene oxide quantum dots. Moreover, from FIG. 2 and FIG. 3, it can be understood that the use of the nitrogen-doped graphene oxide quantum dots can produce almost the same concentration of the free radicals at 5 Gy and at low intensity energy source (such as visible light, infrared light, etc.), this result also indicate that the semiconductor quantum dots have potential in the relevant fields of human therapeutic application or diagnostic application.

The various semiconductor quantum dot obtained from the abovementioned embodiments can be applied to label the cells with different colors. FIGS. 4a to 4f show the images of the photoluminescence reaction by using different sizes of the amino-nitrogen-doped graphene oxide quantum dots obtained from the Embodiment 3-2 in lung cancer cells observed with multi-photon fluorescence microscope. After treating the lung cancer cells with different sizes of amino-nitrogen-doped graphene oxide quantum dots in 50 mg/L for 24 hours, the lung cancer cells is clearly observed to be the color of red (FIG. 4a) to blue (FIG. 4f), and thus the semiconductor quantum dot can be used for different color labeling of cells, which has potentials in effective diagnosis of diseases.

Figure 5A:
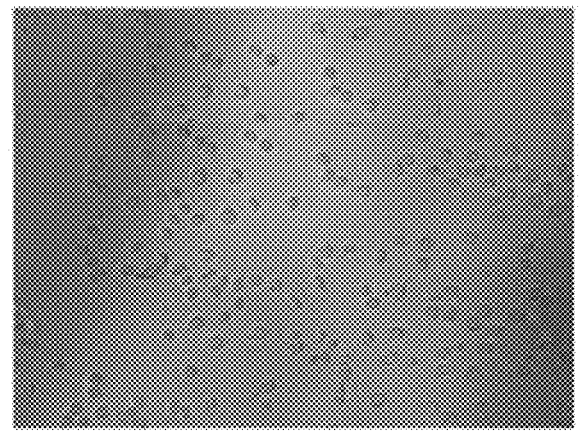
FIGS. 5a to 5j show fluorescence intensity changes of the lung cancer cells labeled by the amino-nitrogen-doped graphene oxide quantum dots ($NH_2$-NGOQD) of the Embodiment 3-1 and the traditional fluorescence dyes (CellVue dye) before exciting and after continuously exciting for 30, 60, 90 mins with a blue light source.
Figure 5B:
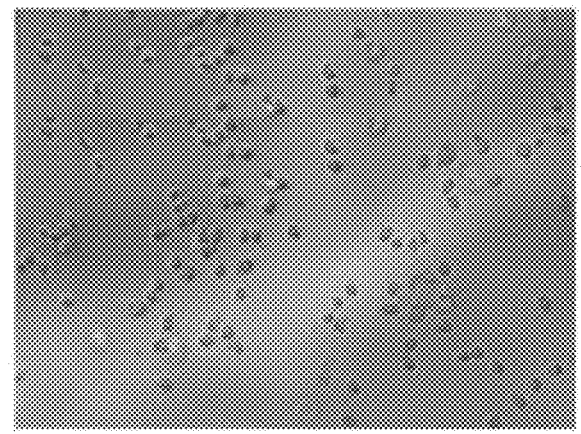
Figure 5C:
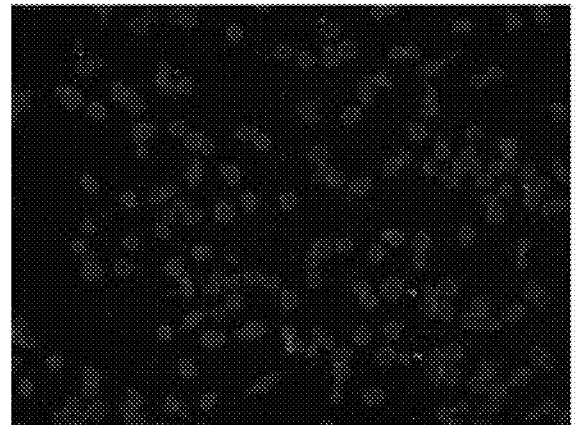
Figure 5D:
Figure 5E:
Figure 5F:
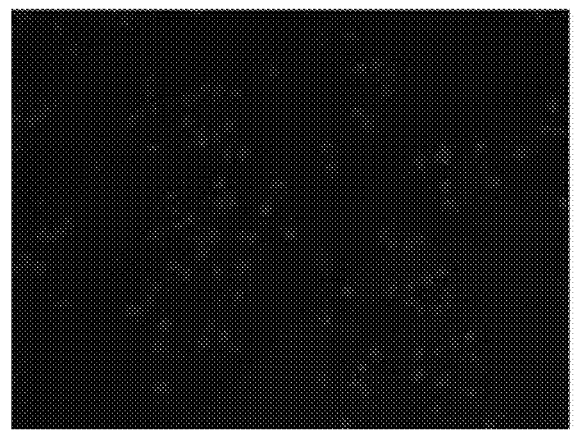
Figure 5G:
Figure 5H:
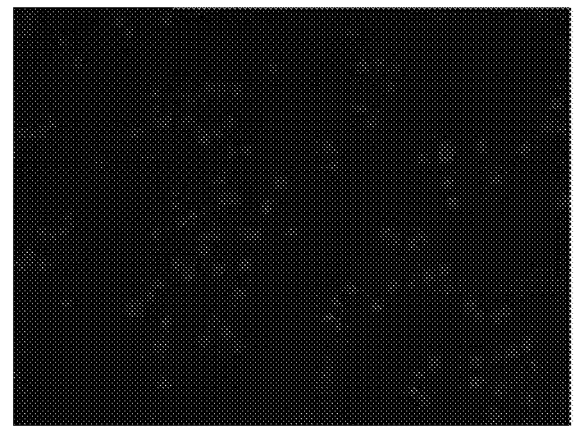
Figure 5I:
Figure 5J:
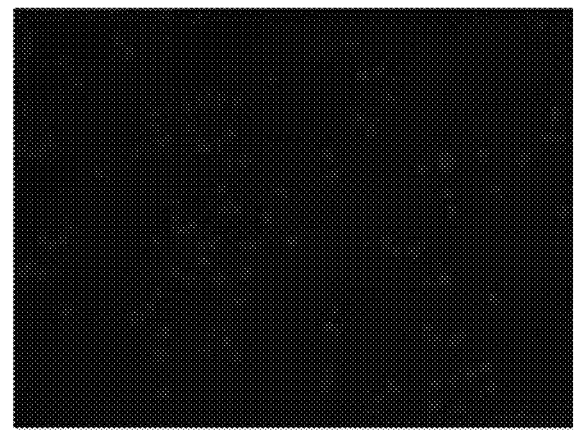

As shown in FIGS. 5a to 5j, the semiconductor quantum dot has higher stability compared with the traditional fluorescence dyes. FIGS. 5a and 5b, respectively shows the lung cancer cells treated with the traditional fluorescence dye (CellVue dye) or the amino-nitrogen-doped graphene oxide quantum dots of the Embodiment 3-1. FIGS. 5c, 5e, 5g, and 5i respectively shows the fluorescence signal of the lung cancer cells labeled by the traditional fluorescence dye (CellVue dye) before excitation, and excitation for 30, 60, 90 mins, wherein the fluorescence signal in FIG. 5e is weakened significantly, and the fluorescence signals in FIGS. 5g and 5i are almost disappeared. However, in FIGS. 5d, 5f, 5h, 5j, compared to the fluorescence signal before excitation (FIG. 5d), after excitation for 30, 60, 90 mins, the fluorescence signal of the lung cancer cells labeled by the amino-nitrogen-doped graphene oxide quantum dots of the Embodiment 3-1 are reduced slightly (FIGS. 5f, 5h, 5j). This result shows that the semiconductor quantum dot has higher stability compared with the traditional fluorescence dyes.

Figure 6:
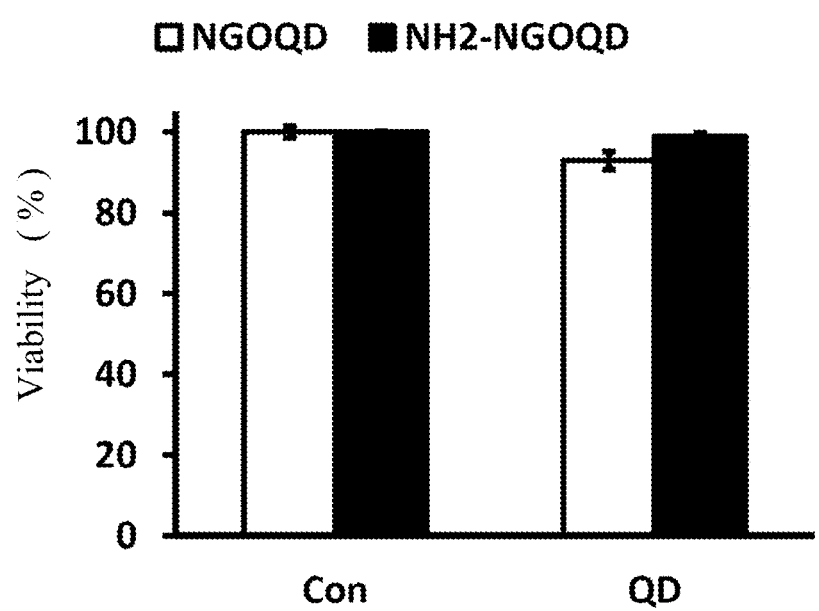
FIG. 6 shows the viability of the cells treated in the concentration of 50 mg/L with the nitrogen-doped graphene oxide quantum dots (NGOQD) of the Embodiment 2-1 or the amino-nitrogen-doped graphene oxide quantum dots (NH2-NGOQD) of the Embodiment 3-1 for 72 hours.

As shown in FIG. 6, the nitrogen-doped graphene oxide quantum dots of the Embodiment 2-1 (NGOQD), or the amino-nitrogen-doped graphene oxide quantum dots of the Embodiment 3-1 ($NH_2$-NGOQD) is used in cells with a high concentration of 50 mg/L, the cell viability is not affected after cultivating for 72 hours. That shows the features of low bio-toxicity.

Figure 7A:
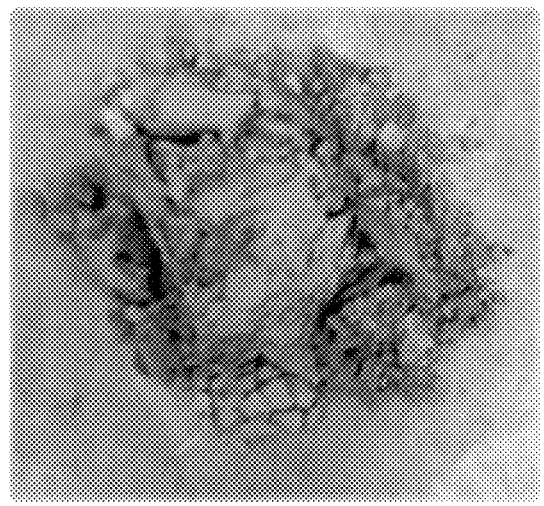
FIGS. 7a to 7e show the generation efficiency of hydrogen gas from decomposing ammonia ($NH_3$) by the boron-and-nitrogen-doped graphene oxide quantum dots (N-BGOQD.
Figure 7B:
Figure 7C:
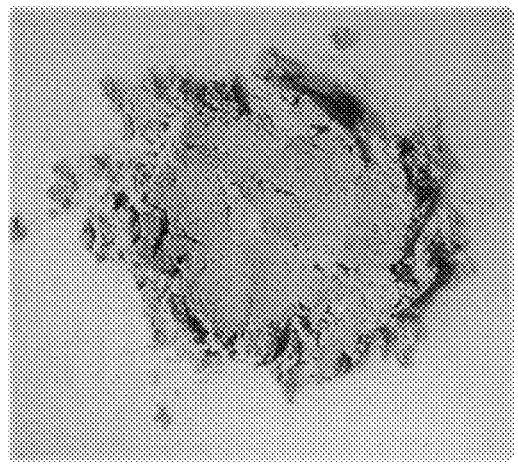
Figure 7D:
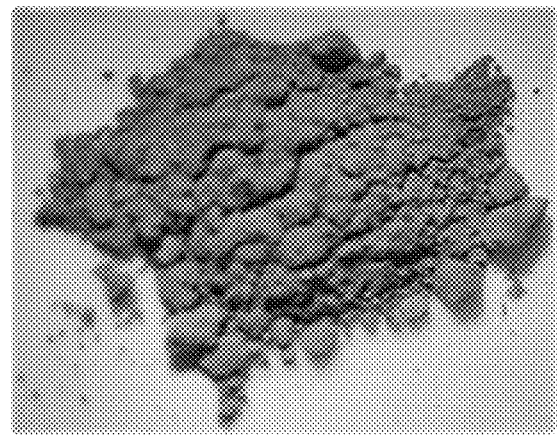
Figure 7E:
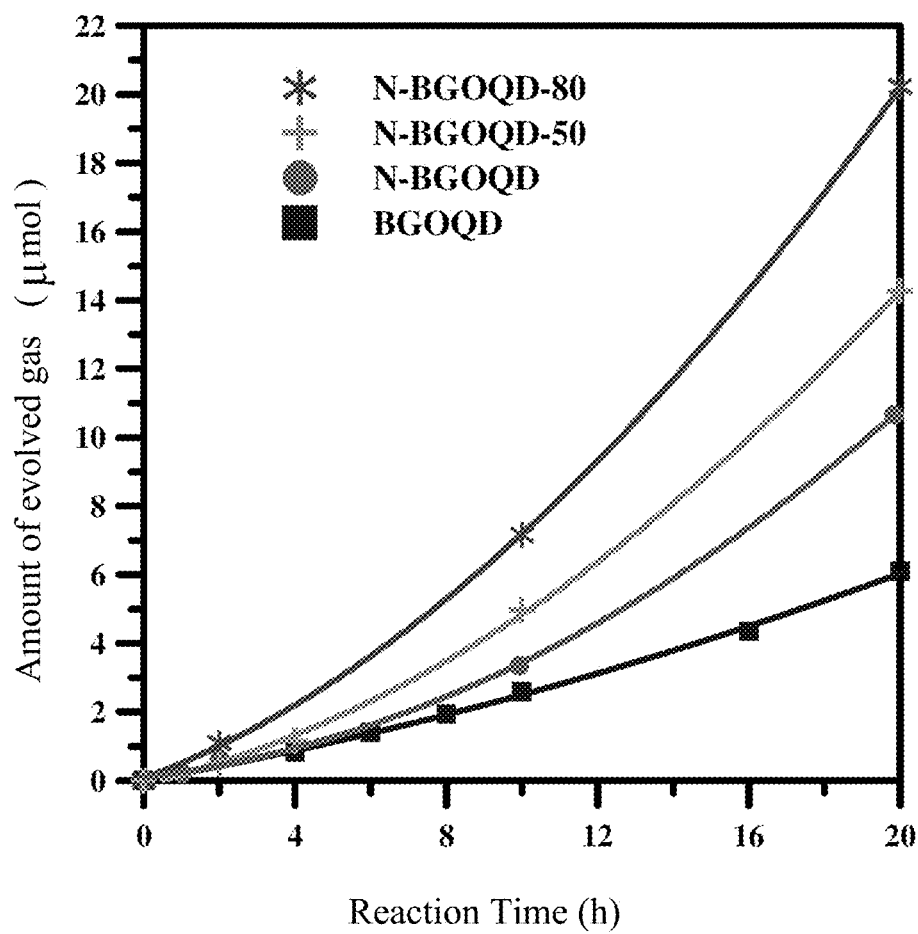

As shown in FIGS. 7a to 7e, the boron-and-nitrogen-doped graphene oxide quantum dots according to the Embodiment 2-4 of the present invention (N-BGOQD: FIGS. 7a to 7c), and the boron-doped graphene oxide quantum dots according to the Embodiment 2-2 (BGOQD: FIG. 7d) can decompose ammonia ($NH_3$) efficiently and generate hydrogen gas under an ultraviolet light (FIG. 7e). The semiconductor quantum dots indeed have the ability for treating the contaminants.

Figure 8:
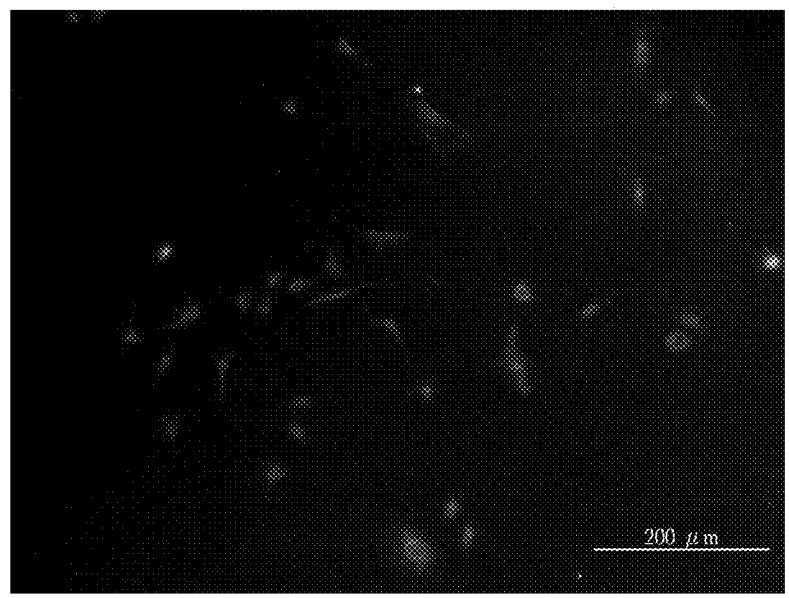
FIG. 8 shows the cell labeled by the semiconductor quantum dot conjugated antibody (conjugating via the functional groups on the semiconductor quantum dot).

A fluorescent secondary antibody is formed by connecting the NH2 group on the aminio-nitrogen-doped graphene quantum dots from the Embodiment 3-1 and a secondary antibody of anti-mouse IgG. The fluorescent secondary antibody is used for fitting with a specific primary antibody of mouse anti-human β-actin to detect β-actin protein expression in lung cancer cells with fluorescence microscope. As shown in FIG. 8, the protein expression of the β-actin in the cells can be detected specifically by the fluorescence signals, which shows that the semiconductor quantum dot has potentials in the application of effective diagnosis of disease.

Compared with the traditional metal semiconductor quantum dot, the semiconductor quantum dot according to the present invention can extend or shorten the absorption wavelength, and have multi-photon reaction. In addition, the semiconductor quantum dot according to the present invention can exert photochemical reaction and photoluminescence properties with high stability, and low bio-toxicity. The semiconductor quantum dot is very suitable for biomedical use, application of green energy source, and contaminant treatment. In addition, the high efficient fluorescent with multi-colors, the redox ability, and stability can be obtained by surface modification (with dopant or functional group) and size adjustment.

The present invention has been described with preferred embodiments thereof and it is understood that many changes and modifications to the described embodiments can be carried out without departing from the scope and the spirit of the invention that is intended to be limited only by the appended claims.

What is claimed is:

1. A method of carrying out a chemical reaction by using a semiconductor quantum dot, comprising steps of:
   (1) mixing a target sample and the semiconductor quantum dot, wherein the semiconductor quantum dot comprises oxidized graphene oxide and has a particle size ranging from 0.3 to 100 nm; and
   (2) providing the semiconductor quantum dot with a predetermined energy, so that the semiconductor quantum dot generates electron-hole pairs, and a redox reaction of the target sample is carried out by the electron-hole pairs; or the target sample or a surrounding molecule thereof generates an active substance, and a redox reaction of the target sample is carried out by the active substance.

2. The method according to claim 1, wherein the semiconductor quantum dot comprises at least one dopant.

3. The method according to claim 2, wherein the dopant is selected from at least one of group IIIA element, group IVA element, group VA element, group VIA element, and transition element having an empty d orbital.

4. The method according to claim 2, wherein the dopant is at least one of O, N, P, B, Fe, Co, and Ni.

5. The method according to claim 2, wherein the dopant has a doping ratio more than 0 mol % and less than 50 mol %.

6. The method according to claim 1, wherein the semiconductor quantum dot is disc-shaped, and has a thickness ranged from 0.1 nm to 10 nm.

7. The method according to claim 1, wherein the semiconductor quantum dot has a surface with at least one functional group selected from H, a group-VA-element functional group, or a group-VIA-element functional group.

8. The method according to claim 7, wherein the group-VA-element functional group is an amino group, P, or a phosphate group.

9. The method according to claim 7, wherein the group-VIA-element functional group is hydroxyl, carbonyl, carboxyl, or acyl.

10. The method according to claim 1, wherein the predetermined energy is provided by a laser, a mercury lamp, a visible light, an ultraviolet light, an infrared light, an endoscopic light, an X-ray, an ultrasound, an electric field, a magnetic field, a nuclear magnetic resonance, or a light-emitting diode in the step (2).

11. The method according to claim 1, wherein the redox reaction in the step (2) comprises decomposition of the target sample, polymerization of the target sample, activation of the target sample, or deactivation of the target sample.

12. The method according to claim 11, wherein the active substance is a free radical or a peroxide.

13. The method according to claim 12, wherein the free radical is $O_2$ or $OH$.;
and the peroxide is $H_2O_2$.

14. The method according to claim 1, wherein the target sample is selected from biological cells, bacteria, viruses, parasites, cell secretions, biological molecules, an organic compound, or an inorganic compound.

15. The method according to claim 14, wherein the organic compound is an aromatic compound, alcohol, aldehyde, ketone, acid, amine, urea, or a polymer thereof.

16. The method according to claim 14, wherein the inorganic compound is water, nitrite, nitrate or ammonia.

17. The method according to claim 14, wherein the biological molecules are peptides, nucleic acids, lipids, carbohydrates, vitamins, hormones, or a polymer thereof.

18. The method according to claim 14, wherein the cell secretions are extracellular vesicles or extracellular matrix.

* * * * *